United States Patent [19]
Kajzar et al.

[11] Patent Number: 4,795,255
[45] Date of Patent: Jan. 3, 1989

[54] APPARATUS AND PROCESS FOR MEASURING NON-LINEAR ORDER THREE OPTICAL CHARACTERISTICS IN AN ISOTROPIC PHASE

[75] Inventors: Francois Kajzar, Voisins Le Bretonneux; Jean Messier, Gif Sur Yvette, both of France

[73] Assignee: Commissariat A L'Energie Atomique, Paris, France

[21] Appl. No.: 100,977

[22] Filed: Sep. 25, 1987

[30] Foreign Application Priority Data
Oct. 3, 1986 [FR] France .................. 86 13838

[51] Int. Cl.⁴ .......................................... G01N 21/63
[52] U.S. Cl. ................................ 356/318; 356/417
[58] Field of Search ................ 356/317, 318, 417

[56] References Cited
PUBLICATIONS

Applied Physics B, vol. 32, 1983, pp. 137–143.
Optics Communications, vol. 56, No. 1, Nov. 1985, pp. 67–72.
Applied Optics, vol. 14, No. 6, Jun. 1975, pp. 1447–1451.
Physical Review A, vol. 32, No. 4, Oct. 1985, pp. 2352–2363.

*Primary Examiner*—F. L. Evans
*Attorney, Agent, or Firm*—Nutter, McClennen & Fish

[57] ABSTRACT

Apparatus and process for measuring optical, non-linear, harmonic emission characteristics of an isotropic phase: susceptibility coefficient, phase displacement and dispersion. Use is made of a beam converging in a first prism and diverging in a second prism after having been focused in the isotropic phase which it traverses over a distance variable as a function of the aperature angle $\alpha$.

6 Claims, 2 Drawing Sheets

APPARATUS AND PROCESS FOR MEASURING NON-LINEAR ORDER THREE OPTICAL CHARACTERISTICS IN AN ISOTROPIC PHASE

BACKGROUND OF THE INVENTION

The present invention relates to an apparatus and to a process for measuring non-linear order three optical characteristics in an isotropic phase: susceptibility coefficient of order three and dispersion of indices.

The appearance of an order three light harmonic can be brought about by exciting a transparent body with the aid of a high intensity light beam, such as that produced by a laser. The energy supplied by the photons to the electrons of the body is in part restored in the form of order three harmonic light radiation with a highly non-linear intensity as a function of the exciting intensity and which is proportional to the square of a so-called order three susceptibility coefficient which is dependent on the material.

However, apparatuses aiming at measuring the characteristics of a body with respect to said order three harmonic emission are confronted with difficult precision problems, because the emission intensity also varies greatly as a function of the thickness traversed by the light beam with a period equal to that which is called the coherence length $l_c = \lambda_\omega / 6(n_{3\omega} - n_{107})$, in which $\lambda_\omega$ designates the wavelength of the incident light of pulsation $\omega$ and in which $n_\omega$ and $n_{3\omega}$ designate the refractive indices of the body at pulsation lights $\omega$ and $3\omega$. This length is usually approximately 1 to 10 micrometers. The problem is even more difficult when working e.g. on liquid phases, which make the light pass through two walls of a tank containing the liquid to be analyzed. The harmonic three radiation collected is then the sum of the harmonic radiation emitted by the liquid and the products thereof by the walls, without it being possible to easily distinguish them.

Thus, an apparatus is known (Meredith, Buchalter, Hanzlik, Journal of Chemistry and Physics No. 78, p. 1533), according to which a parallel light beam passes through a tank of variable width filled by the body, whose characteristics are to be measured. This thickness of the tank walls is variable. The measurement consists of moving the light beam with respect to the tank, so as to traverse continuously variable thicknesses of walls and liquid. The light intensity of third harmonic varies and passes through maxima, whose height and periodicity make it possible to determine the dispersion of the liquid ($n_{3\omega} - N_\omega$), as well as its non-linear susceptibility by comparison with a reference test on a body having known characteristics.

This process involves the creation of complicated interferences, which can only be dealt with by a computer. It is necessary to have a high accuracy on the angles characterizing the geometry of the apparatus and an excellent planeity of the surfaces of the tank walls.

An identical apparatus has been proposed (Thalhammer and Penzhofer, Applied Physics B32, p. 137), but whose walls have a constant thickness and are equal to an even multiple of the coherence length of the material of said walls with respect to the incident light. By forming a vacuum between these two walls, it is possible to show that they are together only able to emit a negligible third harmonic light intensity. However, this conclusion is again open to question if their gap is no longer occupied by the vacuum. The manfacture of walls with a perfect planeity and known thickness in a very accurate manner makes this process virtually unusable in practice, particularly as the coherence length is dependent on the light wavelength and consequently makes it possible to work with light having a given color. According to a third apparatus (Meredith, Buchalter and Hanzlik, Journal of Chemistry and Physics, No. 78, p. 1543), the liquid is disposed between two relatively well spaced walls, whose inner surfaces are parallel. However, the outer surface of the wall by which the light beam enters the apparatus is oblique with the result that the thickness of said wall is variable.

The beam is focused onto said wall and, as hereinbefore, the process consists of moving the beam along the apparatus. The third harmonic emitted has a variable intensity, because it is dependent on the thickness of the window. The harmonic emitted by the passage in the liquid remains constant, because it can be assumed that the liquid thickness is invariable. Even if the window by which the beam passes out is slightly oblique, this imprecision can be ignored, because the divergent beam is wide (low surface intensity) at this point and produces no non-linear intensity harmonic emission.

It is therefore very easy to determine the magnitude of the third harmonic emitted by the light, but the susceptibility coefficient can only be calculated on knowing the dispersion ($n_{3\omega} - n_\omega$) of the liquid after performing another experiment. Thus, this simple and accurate apparatus is not complete. Moreover, it is less generally used than the previous apparatuses, because it uses a greater liquid thickness and which is consequently more opaque.

Moreover, these three apparatuses must be placed in a vacuum chamber, because the light beam is parallel or focused close to the surface of the apparatus, so that the external medium is at least locally traversed by an intense beam. Thus, an atmosphere would also emit a third harmonic, which would falsify the results no matter what the apparatus used.

Thus, in the state of the art these is no apparatus making it possible to analyse the third harmonic optical emission characteristics of a body in a simple, precise and economic manner.

SUMMARY OF THE INVENTION

The present invention obviates the disadvantages referred to hereinbefore in the prior art apparatuses and gives details of the characteristics with the aid of an apparatus placed in the ambient atmosphere and constituted by two quasi-contiguous and slightly oblique thick walls, between which is placed the body or substance to be analyzed and through it is passed a convergent-divergent beam.

More specifically it relates to an apparatus for measuring order three non-linear optical characteristics in an isotropic phase having a convergent-divergent monochromatic beam, two prisms traversed by the beam and separated by a prismatic gap filled by the isotropic phase, transparent to the light of the beam and to the third harmonic of said light, a means for measuring the intensity of the third harmonic of the light of the emitted beam by the passage of said beam into the prisms and the isotropic phase, a means for displacing said beam relative to the prisms, so as to vary the distance covered by the beam in the isotropic phase, wherein the focusing point of the beam is located in the gap between the prisms and wherein the diameters of the convergent beam at the entrance to the first prism and the divergent beam at the exit from the second prism are much larger than the diameter of the beam at the focusing point.

In preferred manner, the thickness of the prisms traversed by the beam are such that the diameters of the convergent beam at the entrance into the first prism and of the divergent beam at the exit from the second prism are at least five times larger than the diameter of the beam at the focusing point.

It is also very advantageous that one of the prisms is constituted by two layers of different materials and that the apparatus also has a means for passing the beam, traversing a random distance in the isotropic phase, through one or other of the layers of said prism.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
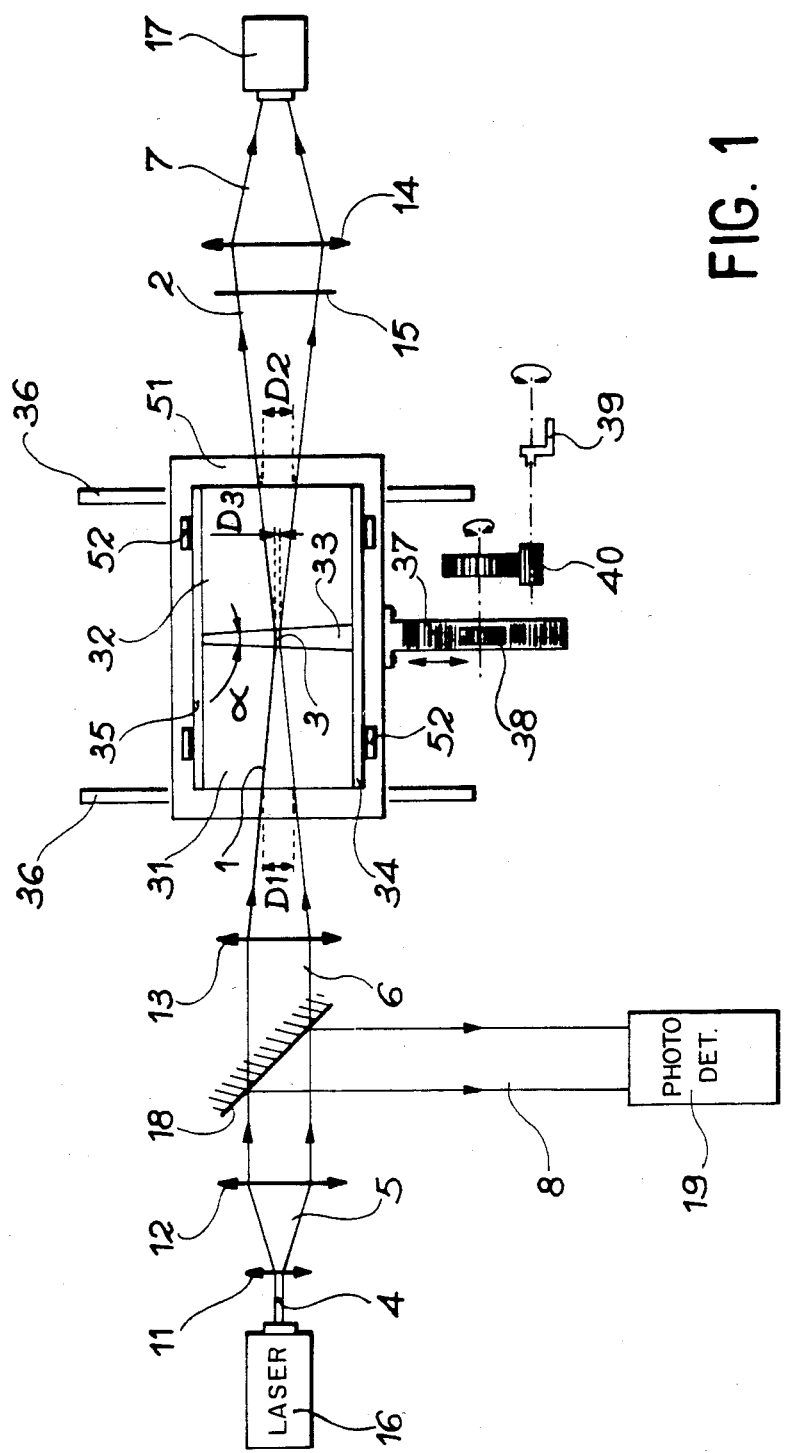
FIG. 1 a plan view of the apparatus according to the invention.

FIG. 1 firstly shows the light beam 1 to 8, which will bring about the emission of the order three or third harmonic. As this phenomenon is non-linear, the beam must be emitted with high intensity, e.g. using a laser 16. The parallel monochromatic radiation 4 of pulsation $\omega$ emitted is firstly made divergent at 5 using a lens 11. A second lens 12 again makes the beam parallel at 6, with a much wider diameter than at 4. This arrangement makes is possible to obtain a smaller surface intensity in the ambient air, which substantially eliminates any third harmonic emission.

At this point, it is possible to position an auxiliary device making it possible to measure the intensity of the beam, such as a photodetector 19, which strikes the beam 8 produced by the deflection of beam 5 by a mirror 18, which is obviously removed to carry out the actual experiment. In a variant, use is made of a semitransparent mirror 18.

According to the invention, the light beam is focused at 3 in isotropic phase 33, whereof it is necessary to measure the characteristics and which fills the gap between two prisms 31, 32 and which is closed at its end by walls 34, 35. This isotropic phase 33 is generally a liquid, but can also be a gas or even a solid with a sufficiently low melting point introduced in the molten state and which is then left to cool.

Another lens 13 is then interposed and this supplies a convergent beam 1, which penetrates prism 31, while still having a relatively large diameter D1 at the entrance and which then penetrates with a much smaller diameter the isotropic phase 33. In this phase, beam 3 is substantially cylindrical and acquires a minimum diameter D3. It then becomes divergent in accordance with reference 2 and enters prism 32, from which it departs with a relatively large diameter D2. According to the invention, D1 and D2 must be significantly larger than D3. Ratios D1/D3 and D2/D3 must always exceed 5 and preferably exceed 10. The beam then passes into a filter 15, which stops the light of pulsation $\omega$. Thus, all that is left is a radiation of pulsation $3\omega$ emitted by the passage of the light beam in prisms 31, 32 and isotropic phase 33 and which is concentrated on a photomultiplier 17 with the aid of a lens 14.

Thus, unlike in the prior art apparatuses, prisms 31, 32 have a significant thickness compared with the distance covered by the light beam in isotropic phase 33. This construction makes it possible to obtain a third harmonic emission in isotropic phase 33 and in the contiguous parts of prisms 31, 32, i.e. where the beam is narrowest and most intense. However, the emission is virtually zero at the ends of prisms 31, 32 and in the ambient air, which explains why there is no need to accurately know the thickness of prisms 31, 32 and why no particular care is required in connection with the planeity of their extreme sufaces. Only the surfaces in contact with the isotropic phase 33 must be prefectly polished. The thickness of prisms 31, 32 traversed by beam 1 or 2 must be adequate to permit an adequate focusing thereof in the isotropic phase 33 and must be large compared with the coherence length of the light beams in prisms 31, 32 (several hundred times greater, i.e. a few centimeters).

Obviously, it is necessary to choose the materials from which the prisms 31, 32 are made in such a way that they are as transparent as possible both for the light of pulsation and for that of pulsation $3\omega$.

The gap in which the isotropic phase 33 is located is wedge or corner-shaped with a very acute aperture or opening angle $\alpha$ of approximately one degree or a fraction of a degree. Moreover, prisms 31 and 32 are quasi-contiguous, so that the thickness of the isotropic phase 33, which can be more or less opaque, remains limited. The need for a wedge-shaped gap will be explained in connection with the description of the use of the apparatus.

The assembly essentially constituted by prisms 31, 32 and the isotrophic phase 33 is mobile perpendicular to the direction of beam 1 to 8, so that the latter traverses a continuously variable thickness of the isotropic phase 33. A random mechanical system can be used and e.g. rails or slides 36 are shown, along which moves the carriage or trolley 51 carrying prisms 31, 32 and which stops their transverse deflection or travel by using stops or abutments 52 shown more clearly in FIG. 2. The carriage is moved by means of a belt or chain 37 actuated by a wheel 38 linked with a crank 39 or driven automatically under the control of a computer. It is also possible to introduce a gear train 40 for gearing down the movement.

During the displacement of carriage 51, it can be seen that the intensity of the third harmonic light emitted and collected by photomultiplier 17 is variable and periodic. It can be demonstrated that the period p corresponding to a thickness variation of the isotropic phase 33 traversed by the beam is equal to the coherence length lc of said phase by the relation $p \times tg\alpha = lc$, in which $lc = \lambda_\omega/6(n_{3\omega} n_\omega)$ in which $\lambda_\omega$ designates the wavelength of the light of pulsation $\omega$, which can be easily determined. Thus, the displacement of carriage 51 makes it possible to obtain information on the dispersion $(n_{3\omega} - n_\omega)$ of the isotropic phase 33, provided that its travel is adequate to make it possible to measure one period or cycle of the phenomenon.

It is possible to deduce the third harmonic non-linear susceptibility coefficient $\chi_L^{(3)}$ of the isotropic phase 33 which the aid of the dispersion whose obtention process has just been indicated, from the maximum intensity of the third harmonic light measured, the characteristics of the material constituting the prisms 31, 32 and a calibration test on another isotropic phase L, whose characteristics are known. Thus, if the refractive indices of the different materials do not differ excessively and if the prisms 31 and 32 are made from the same material $$I_L/I_{L'} = [(\rho_p - \rho_L)/(\rho_p - \rho_{L'})] \text{ in which}$$
$$\rho_i = \chi_i^{(3)}/(n_{3\omega}^2 - n_\omega^2)_i$$

in which L designates the isotropic phase 33, L' the calibration isotropic phase, p the material from which prisms 31,32 are made and $I_j$ the maximum third order light intensity found during the displacement of the carriage 51, body j filling the gap between prisms 31 and 32.

Figure 2:
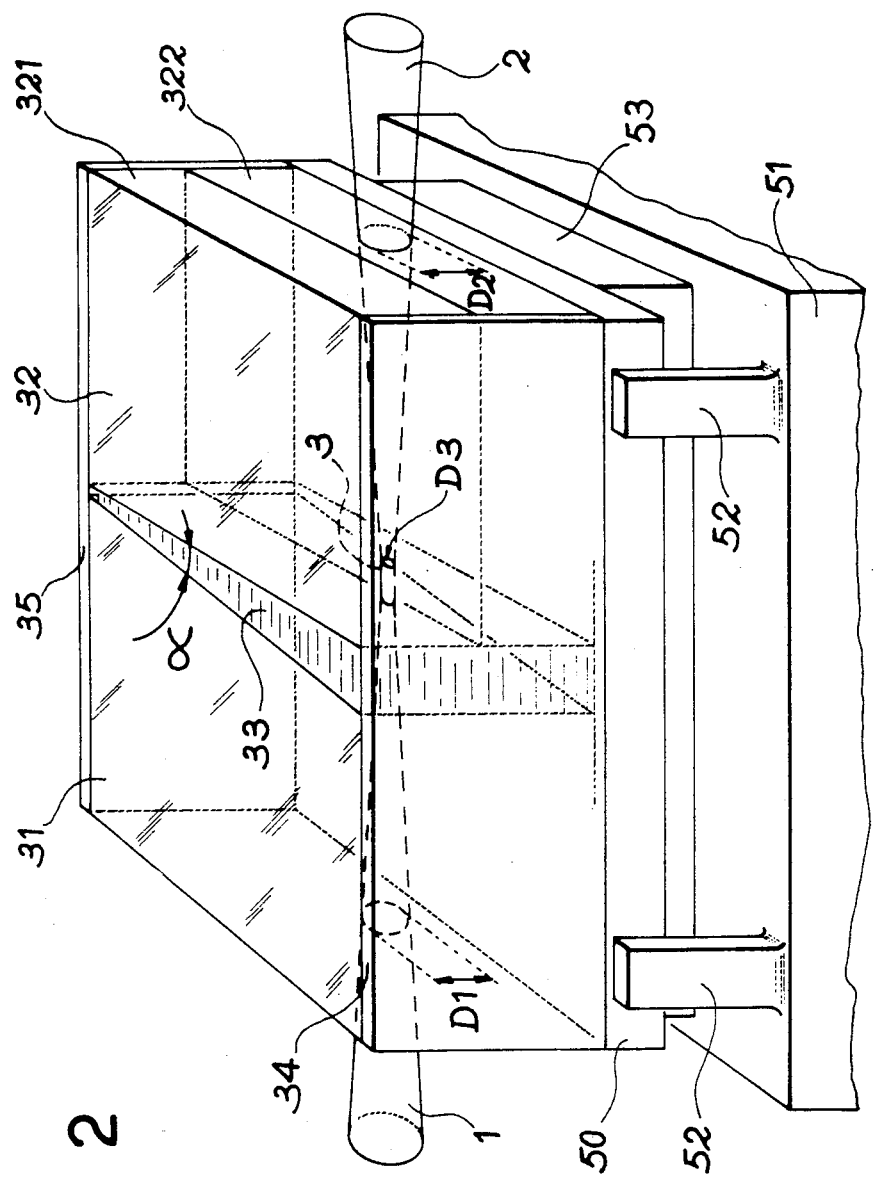
FIG. 2 a partial perspective view of the invention.

Another important feature of the invention will now be described relative to FIG. 2. It can be seen that the exit prism of beam 32 is divided into two superimposed layers 321 and 322 made from two different materials. These layers are sufficiently thick to enable each to contain the divergent beam 2, which can be passed through one or other of these by means of a shim 53, which can be positioned between the carriage 51 and the bottom 50 of the apparatus mainly constituted by prisms 31 and 32.

The usefulness of this division of prism 32 is apparent on exposing the isotropic phase 33 to a light beam making it necessary to operate around an absorption band or a forbidden transition. The emission of the third harmonic is then phase displaced by an angle $\phi$ and it is necessary to write the non-linear susceptibility coefficient is complex form $|\chi_L^{(3)}|xe^{i\phi}$. Thus, the equations given hereinbefore and making it possible to deduce $\chi_L^{(3)}$ as a function of $I_L$ no longer apply, more especially as the general shape of curve $I_L$ as a function of the lateral displacement of carriage 51 is not modified and it is not possible to diagnose the phase displacement by the mere appearance of said curve.

Therefore a complementary measurement has to take place, which explains the subdivision of prism 32 into two layers 321,322. With the aid of shim 53 the light beam 2 is in turn passed through layer 321 and layer 322 and on each occasion the third harmonic light intensity variation is established by displacement of carriage 51, as described hereinbefore.

In the case of a phase displacement of the non-linear susceptibility coefficient $I_L$, the two plotted intensity curves are different both for the amplitude of the periodic variations and for the phase of the minima. This double information consequently makes it possible to obtain the modulus and the phase of the non-linear susceptibility coefficient.

The materials constituting the layers 321,322 of prism 32 must both differ from that constituting prism 31. However, for reasons of simplicity, preference is given to the use of the material of prism 31 for one of the two layers of prism 32.

Thus, this apparatus differs greatly from the prior art to the extent that it is possible to carry out measurements in the ambient air and use is made of a convergent-divergent beam focused on the isotropic phase 33 and which traverses two thick prisms 31,32. The juxtaposing of two layers 321,322 of different materials for prism 32 is also an original contribution of the invention, because none of the known apparatuses have provided a simple means for measuring the possible phase displacement of the non-linear susceptibility coefficient $\chi^{(3)}$ of the isotropic phase 33.

What is claimed is:

1. An apparatus for measuring third order non-linear optical characteristics in an isotropic phase incorporating means for producing a convergent-divergent monochromatic light beam of pulsation $\omega$ and having a focusing point, two prisms, traversed by the beam and separated by a prismatic gap filled by the isotropic phase, the prisms and the isotropic phase being formed from materials transparent to the light of the beam and to the third harmonic of said light, a means for displacing the beam with respect to the prisms, so as to vary the distance covered by the beam in the isotropic phase and a means for measuring the third harmonic intensity of the light emitted by the passage of the beam in the prisms and the isotropic phase, wherein the focusing point of the beam is located in the gap between the prisms and wherein the diameters of the convergent beam at the entrance into the first prism and of the divergent beam at the exit from the second prism are much larger than the diameter of the beam at the focusing point.

2. An apparatus for measuring the third order non-linear optical characteristics in an isotropic phase according to claim 1, wherein the diameters of the convergent beam at the entrance into the first prism and the divergent beam at the exit from the second prism are at least five times larger than the diameter of the beam at the focusing point.

3. An apparatus for measuring the third order non-linear optical characteristics in an isotropic phase in accordance with claim 1, wherein one of the prisms is formed from two layers of different materials and wherein said apparatus comprises a means for passing the beam, covering a variable distance in the isotropic phase, through one or the other of the layers of the prism.

4. An apparatus for measuring the third order non-linear optical characteristics in an isotropic phase according to claim 3, wherein one of the materials of the prism, which has two materials, is the material from which the other prism is made.

5. A process for measuring the third order non-linear optical characteristics in an isotropic phase with the aid of an apparatus incorporating means for producing a convergent-divergent monochromatic light beam of pulsation $\omega$ and having a focusing point, two prisms traversed by the beam and separated by a prismatic gap filled by the isotropic phase, the prisms and the isotropic phase being formed from materials transparent to the light of the beam and to the third harmonic of said light, a means for displacing the beam relative to the prisms, so as to vary the distance covered by said beam in the isotropic phase and a means for measuring the third harmonic intensity of the light emitted by the passage of the beam in the prisms and the isotropic phase, wherein the focusing point of the beam is located in the gap between the prisms and wherein the diameters of the convergent beam at the entrance into the first prism and of the divergent beam at the exit from the second prism are much larger than the diameter of the beam at the focusing point, characterized in that said process comprises continuously displacing the position of the prisms with respect to the beam, so that it passes through a distance in the isotropic phase varying by at least the third order coherence length corresponding to said phase and the light of the beam and detecting variations in said measured light intensity as a function of the path of the beam with the aid of a means for deducing therefrom the susceptibility coefficient $\chi^{(3)}$ and/or the dispersion $(n_{3\omega} - n_\omega)$ of the isotropic phase by comparison with a reference curve.

6. A process for measuring the third order non-linear optical characteristics in an isotropic phase with the aid of the apparatus incorporating means for producing a convergent-divergent monochromatic light beam of pulsation $\omega$ and having a focusing point, two prisms traversed by the beam and separated by a prismatic gap filed by the isotropic phase, the prisms and the isotropic phase being formed from materials which are transparent to the light of the beam and to the third harmonic of said light, a means for displacing the beam with respect to the prisms, so as to vary the distance covered by said beam in the isotropic phase and a means for measuring the third harmonic intensity of the light emitted by the passage of the beam in the prisms and the isotropic phase, wherein the focusing point of the beam is located in the gap between the prisms and wherein the diameters of the convergent beam at the entrance into the first prism and of the divergent beam on leaving the second prism are much larger than the diameter of the beam at the focusing point, wherein one of the prisms is constituted by two layers of different materials, wherein said apparatus comprises a means for passing the beam, traversing a variable distance in the isotropic phase, through one or the other of the layers of said prism, characterized in that said process comprises effecting the operation of continuously displacing the position of the prisms with respect to the beam, so as to make it pass through a distance in the isotropic phase varying by at least the third order coherence length corresponding to said phase and to the light of the beam, the beam also passing into only one of the layers of the prism, which has two layers, followed by the repetition of this operation, the beam on this occasion passing into the other layer of the beam and detecting variations in said measured light intensity as a function of the path of the beam with the aid of means for deducing therefrom the susceptibility coefficient $\chi^{(3)}$ and/or the dispersion $(n_{3\omega} - n_\omega)$ of the isotropic phase by comparison with a reference curve and comparing the two measured layers in order to deduce thereform the phase displacement angle $\phi$ of the susceptibility coefficient $\chi^{(3)}$.

* * * * *